United States Patent [19]

Lin et al.

[11] Patent Number: 5,324,503
[45] Date of Patent: Jun. 28, 1994

[54] IODO-PHENYLATED CHELATES FOR X-RAY CONTRAST

[75] Inventors: Youlin Lin; Muthanadar P. Periasamy, both of Chesterfield; Donald R. VanDeripe, St. Louis, all of Mo.

[73] Assignee: Mallinckrodt Medical, Inc., St. Louis, Mo.

[21] Appl. No.: 832,148

[22] Filed: Feb. 6, 1992

[51] Int. Cl.$^5$ ............ A61K 49/04; A61K 31/66; A61K 31/30; A61K 31/295

[52] U.S. Cl. ............................ 424/5; 424/9; 436/173; 436/806; 128/653.4; 128/654; 514/6; 514/114; 514/119; 514/492; 514/499; 514/501; 514/502; 534/16; 556/1; 556/44; 556/19; 556/50; 556/63; 556/107; 556/116; 556/134; 556/148

[58] Field of Search ............ 424/5, 9; 436/173, 806; 128/653.4, 654; 514/114, 119, 492, 499, 501, 502, 6; 534/16; 556/19, 50, 63, 107, 116, 134, 148, 1, 44

[56] References Cited

U.S. PATENT DOCUMENTS

| | | | |
|---|---|---|---|
| 4,125,599 | 11/1978 | Wiegert | 424/5 |
| 4,125,709 | 11/1978 | Smith | 536/53 |
| 4,138,589 | 2/1979 | Wiegert | 562/434 |
| 4,230,845 | 10/1980 | Smith | 536/4 |
| 4,396,598 | 8/1983 | Lin | 424/5 |
| 4,714,607 | 12/1987 | Klaveness | 424/9 |
| 4,880,008 | 11/1989 | Lauffer | 128/654 |
| 4,885,363 | 12/1989 | Tweedle et al. | 540/465 |
| 4,916,170 | 4/1990 | Nambu et al. | 523/137 |
| 4,980,502 | 12/1990 | Felder et al. | 562/444 |
| 5,013,831 | 5/1991 | Stavrianopoulos | 536/27 |
| 5,019,371 | 5/1991 | Lin et al. | 424/5 |
| 5,075,502 | 12/1991 | Kneller et al. | 564/153 |
| 5,114,703 | 5/1992 | Wolf et al. | 424/5 |

FOREIGN PATENT DOCUMENTS

| | | |
|---|---|---|
| 1064988 | 1/1988 | Australia . |
| 0284549 | 9/1988 | Fed. Rep. of Germany . |

OTHER PUBLICATIONS

Ainscough, E. W. et al *J. Chem. Soc.* (Dalton Trans. 8) 1701-7 (1981).
Whiting, R. F. et al. *Angew. Chem.* 86(16):587-8 (1974).

*Primary Examiner*—Gary E. Hollinden
*Attorney, Agent, or Firm*—Rita Downard Vacca

[57] ABSTRACT

Hybrid agents for enhancing in vivo diagnostic imaging of body organs and tissues, and methods of preparing and using the same.

6 Claims, No Drawings

1

IODO-PHENYLATED CHELATES FOR X-RAY CONTRAST

This invention relates to novel agents for enhancing diagnostic imaging and more particularly to novel compositions, methods of preparing the compositions and methods of using the compositions for enhancing both x-ray images and magnetic resonance images for in vivo diagnostic imaging of body organs and tissues.

BACKGROUND OF THE INVENTION

The techniques of magnetic resonance imaging (MRI) encompass the detection of certain atomic nuclei utilizing magnetic fields and radio-frequency radiation. MRI is similar in some respects to x-ray computed tomography (CT) in providing a cross-sectional display of the body organ anatomy with excellent resolution of soft tissue detail. In current use, the images produced constitute a map of the distribution density of protons and/or their relaxation times in organs and tissues. The MRI technique is advantageously non-invasive as it avoids the use of ionizing radiation.

While the phenomenon of MRI was discovered in 1945, it is only relatively recently that it has found application as a means of mapping the internal structure of the body as a result of the original suggestion of Lauterbur (Nature, 242, 190–191, 1973). The lack of any known hazard associated with the level of the magnetic and radio-frequency fields that are employed renders it possible to make repeated scans on vulnerable individuals. Additionally, any scan plane can readily be selected including transverse, coronal, and sagittal sections.

In a MRI experiment, the nuclei under study in a sample (e.g. protons) are irradiated with the appropriate radio-frequency (RF) energy in a highly uniform magnetic field. These nuclei as they relax subsequently emit RF radiation at a sharp resonant frequency. The emitted frequency (RF) of the nuclei depends on the applied magnetic field.

According to known principles, nuclei with appropriate spin when placed in an applied magnetic field [B, expressed generally in units of gauss or tesla ($10^4$ gauss)] align in the direction of the field. In the case of protons, these nuclei precess at a frequency f=42.6 MHz at a field strength of 1 Tesla. At this frequency, an RF pulse of radiation will excite the nuclei and can be considered to tip the nuclei out of the field direction, the extent of this rotation being determined by the pulse duration and energy. After the RF pulse, the nuclei "relax" or return to equilibrium with the magnetic field, emitting radiation at the resonant frequency. The decay of the signal is characterized by two relaxation times, i.e., $T_1$, the spin-lattice relaxation time or longitudinal relaxation time, that is, time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

It is believed that MRI has a greater potential than CT for the selective examination of tissue characteristics in view of the fact that in CT, the x-ray attenuation coefficients alone determine image contrast whereas at least four separate variables ($T_1$, $T_2$, nuclear spin density and flow) may contribute to the MRI signal. For example, it has been shown (Damadian, Science, 171, 1151, 1971) that the values of the $T_1$ and $T_2$ relaxation in tissues are generally longer by about a factor of two (2) in excised specimens of neoplastic tissue compared with the host tissue.

By reason of its sensitivity to subtle biochemical differences between organs and/or tissues, it is believed that MRI may be capable of differentiating tissue types and in detecting diseases which induce biochemical changes that may not be detected by x-ray or CT which are only sensitive to differences in the electron density of tissue.

Continuing efforts are being made to develop imaging agents for enhancing the images obtained through the use of x-ray techniques as well as MRI techniques. Improved x-ray contrast agents for intravascular and central nervous system visualization are likewise being developed. As is known, for the current triiodobenzene ionic and nonionic x-ray contrast media, the iodine in the molecule provides opacification to the x-rays. The remainder of the molecule provides the framework for the transport of the iodine atoms through the biological system under analysis. However, the structural arrangement of the molecule is important in providing stability, solubility and biological safety in various organs A stable carbon-iodine bond is achieved in most compounds by attaching the iodine molecules to an aromatic nucleus. An enhanced degree of solubility as well as safety is conferred on the molecule by the addition of suitable solubilizing and detoxifying groups.

Several of the features that are desirable for intravascular and central nervous system x-ray contrast agents are often incompatible so that all such agents represent compromises. In searching for the best compromise, the controlling factors are pharmacological inertness, i.e., invivo safety, and high water solubility. Thus, the ideal intravascular or central nervous system agent represents a compromise in an attempt to obtain the following criteria:

1. Maximum opacification to x-rays;
2. Pharmacological inertness;
3. High water solubility;
4. Stability;
5. Selective excretion;
6. Low viscosity; and
7. Minimal osmotic effects.

SUMMARY OF THE INVENTION

The present invention is premised on the realization that contrast media mixtures containing dual K edge absorption bands for x-rays are superior agents for use with fast switching digital subtraction angiographic equipment as well as with other types of imaging equipment of current use. Iodine's K edge is 33 key; K edge values below 33 key tend to be marginal when used as contrast agents due to the limited penetration of biological systems by weaker x-rays. The heavy radiopaque, paramagnetic metal elements with K edge values above that of iodine, are generally highly toxic when administered as salts and therefore must be administered as stable chelates. For this reason, "hybrid" contrast molecules such as those of the present invention and described in detail below are compounds having at least one heavy metal ion which is a paramagnetic metal ion, chelated by a compound having an iodine carrying moiety.

The compounds of the present invention may be used as both x-ray contrast (XRC) agents and magnetic resonance imaging (MRI) agents. The dual nature of these compounds is very beneficial for hospitals having diagnostic centers. The dual nature of the compounds saves on storage space since only one product need be stocked for both XRC and MRI purposes rather than several products. Another advantage of the compounds of the present invention is that in MRI use, the compounds are less toxic than currently known MRI agents. The hydroxyl groups located on the triiodinated portion of the compound greatly increase the compound's hydrophilicity. Additionally, for compounds containing more than one chelating portion, toxicity is greatly decreased. For example, if two chelating portions are present in the compound, half as much need be used to obtain the same quality image. Thereby, since less is used, osmolality is also greatly decreased. Another advantage of the present invention is that in XRC use, less of the agent is used to obtain the same quality image. The heavy metal ion(s), as with iodine, serve to block x-rays thereby allowing one to use less. Because a lesser amount of the compound need be used, it is likewise less toxic and possibly less expensive to use.

Therefore, an object of the present invention is to provide "hybrid" imaging agents containing both iodine and at least one heavy metal ion which can be used as either x-ray contrast or MRI agents.

Another object is to provide "hybrid" imaging agents which permit the use of substantially lower concentrations of the agent with equal or improved visual images over that of currently used MRI or x-ray contrast agents, due to the presence of both iodine and at least one heavy metal ion.

Another object is to provide "hybrid" imaging agents having reduced side effects from that of currently used agents due to the lower concentrations and doses necessary for imaging.

The agents of the present invention may also be used in various radiographic procedures including those involving cardiography, coronary arteriorography, aortography, cerebral and peripheral angiography, orthography, venography, neurography, myelography and similar such uses.

DETAILED DESCRIPTION OF THE INVENTION

The hybrid compounds of the present invention can be either monomeric or polymeric. As used herein, the term monomeric refers to a chelating moiety capable of chelating one metal ion and the term polymeric refers to a chelating moiety capable of chelating more than one metal ion. In either case, the hybrid compounds of the present invention will contain at least one substituent carrying iodine.

Several representative, however not all inclusive, examples of such hybrid compounds are illustrated in formulas 1 through 3 below:

[chelate]—linker—[iodinated moiety]   Formula 1

[chelate]—linker—[iodinated moiety]—linker—[chelate]   Formula 2

[iodinated moiety]—linker—[chelate]—linker—[iodinated moiety]   Formula 3

In the hybrid compounds of the present invention, the chelating moiety generally includes any compound capable of chelating metal ions such as polyamino carboxylic acids, for example, EDTA, DTPA, EhTA, DCTA, DOTA, DO$_3$A, HP-DO$_3$A and TETA, or their derivatives, desferrioxamine derivatives, cryptands, calixarenes, chelating polymers and the like.

The hybrid compound of the present invention may incorporate two chelating moieties in one compound to decrease the osmolality. When two chelating moieties are present, half as much of the agent may be used to obtain the same quality image while simultaneously decreasing osmolality and harmful side effects.

The linker portion of the present invention serves to link the chelating moiety to the iodinated moiety while avoiding, lessening or eliminating steric hinderance between the moieties. The suitable linker likewise prevents interference by the iodinated moiety on the chelating moiety to preserve the chelating capabilities thereof.

The iodinated moiety generally includes substituents having properties which improve the hydrophilicity and toxicity of the hybrid compound. Hydroxyl groups are preferred on the substituents to increase the hydrophilicity of the hybrid compounds. The special properties of various iodinated moieties are described in detail in U.S. Pat. Nos. 4,138,589; 4,125,709; 4,125,599; 5,019,371; 4,230,845; 5,075,502 and 4,396,598 each incorporated herein by reference.

A more specific example of such a hybrid compound is illustrated in structural Formula 4 below

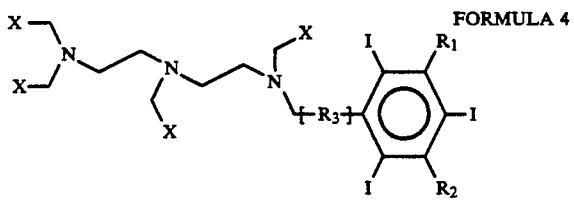

FORMULA 4 wherein

R$_1$ is selected from the group consisting of CONHCH(CH$_2$OH)(CHOHCH$_2$OH), CON(R$_4$)CH$_2$CHOHCH$_2$OH, CON(R$_4$)CH(CH$_2$OH)$_2$, CON(R$_4$)CH$_2$CH$_2$OH, CON(R$_4$)CH$_3$, CONH$_2$, N(R$_4$)COCH$_2$OH, N(R$_4$)COCH$_3$, CO$_2$R$_5$ and suitable linkers for attaching a biomolecule such as N(R$_4$)COCH$_2$— or N(R$_4$)CS—; R$_2$ is selected from the group consisting of R$_1$,

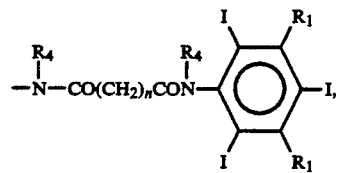

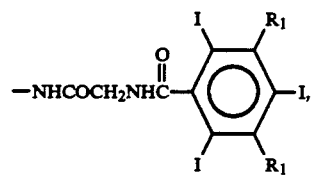

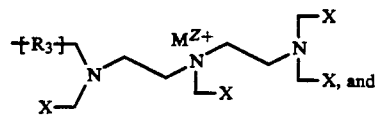

-continued

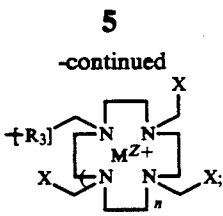

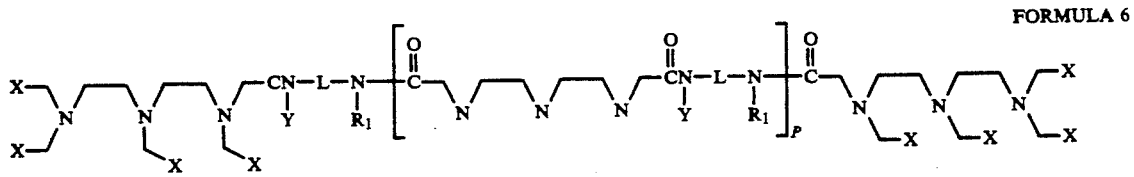

FORMULA 6

$R_3$ is a linker selected from the group consisting of —N($R_4$)CO(CH$_2$)$_m$NHCO, —N($R_4$)CO, CONHCH$_2$(CH$_2$)$_m$NHCO, N($R_4$)COCH$_2$— and N($R_4$)CS—;

$R_4$ is selected from the group consisting of hydrogen, $C_{1-10}$ alkyl, $C_{1-10}$ mono- or poly- hydroxyalkyl and $C_{1-10}$ mono- or poly- alkoxyalkyl;

$R_5$ is selected from the group consisting of cations such as sodium, potassium, meglumine and quaternary ammonium compounds such as NH$_4^+$;

X is a ligand chelating site selected from the group consisting of —CO$_2^-$, CH$_2$S$^-$, —PO$_3^-$, —CONHCH$_2$CHOHCH$_2$OH, —CONHOH, —CONHCH$_2$CO$_2^-$, phenolate and Y;

Y is selected from the group consisting of

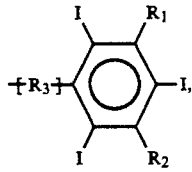

COQ and CONHQ;

Q is selected from the group consisting of biomolecules and polyhydroxyl compounds such as carbohydrates or polylysines;

$M^{z+}$ is a heavy metal ion selected from the group consisting of Bi, Gd, Ba, Gd, Mn, Cu, Cr, Fe, Co, Er, Ni, Eu, Dy, Sc, Ti, V, Mo, Tc, Ru, Ce, Pt, Nd, Pm, Sm, Tb, Ho, Tm and Yb having a valence z of 2+, 3+ or 4+;

n is a whole number less than eleven; m is an integer less than eleven.

Another example of a hybrid compound of the present invention is illustrated in structural FORMULA 5 below.

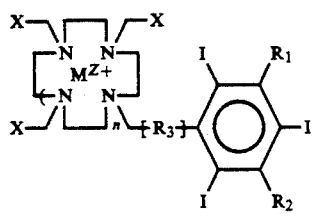

FORMULA 5 wherein $R_1$, $R_2$, $R_3$, $R_4$, $R_5$, Q, X, Y, $M^{z+}$, n and m are the same as respectively defined in FORMULA 4 above.

Still another example of a hybrid compound of the present invention is illustrated in structural FORMULA 6 below wherein $R_1$, $R_2$, $R_3$, $R_4$, $R_5$, Q, $M^{z+}$, n, m, and X are the same as respectively defined in FORMULA 4 above; Y is selected from the group consisting of

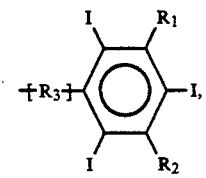

COQ and CONH, wherein at least one Y is

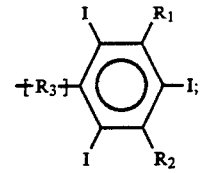

L is a linker selected from the group consisting of —(CH$_2$CH$_2$O)$_n$CH$_2$CH$_2$—, —CH$_2$—(CHOH)-$_n$—CH$_2$—, and —(CH$_2$)$_n$—; and p is an integer designated to describe the polymeric nature of the compound whereby p is an integer of 500 or less but preferably 150 or less.

The hybrid compounds of the present invention can also be attached to a polymeric compound. Examples of such polymeric compounds include biomolecules such as hormones, proteins, lipids, polyhydroxyl compounds such as amino sugars, carbohydrates and polylysines to name a few. The hybrid compounds of the present invention are attached to such a polymeric compound either through the iodine carrying substituent or through the chelating moiety.

The hybrid compounds of the present invention can also be carried by liposomes such as unilamellar or multilamellar vesicles.

The present invention is further directed to methods for making such compounds as set forth in detailed examples below which are meant to be illustrative and are in no way intended to be limiting.

EXAMPLE 1

Preparation of the Hybrid Compound [N,N''-bis{N-[3,5-di(N-(2,3-dihydroxypropyl)carbamoyl)-2,4,6-triiodophenyl]carbamoylmethyl}carbamoylmethyl}diethylenetriamine-N,N',N''-triaceto]-gadolinium (III) (5)

ml. of N,N-dimethylformamide and 20 ml. of dimethyl sulfoxide at 0° C. The reaction mixture is then heated at 80° C. for two days to form an adduct. Following that, the adduct is acidified to pH 3.5 and evaporated to a viscous residue. Purification of crude material using preparative high pressure liquid chromatography (C$_{18}$: stationary phase, water: mobile phase) gives a colorless

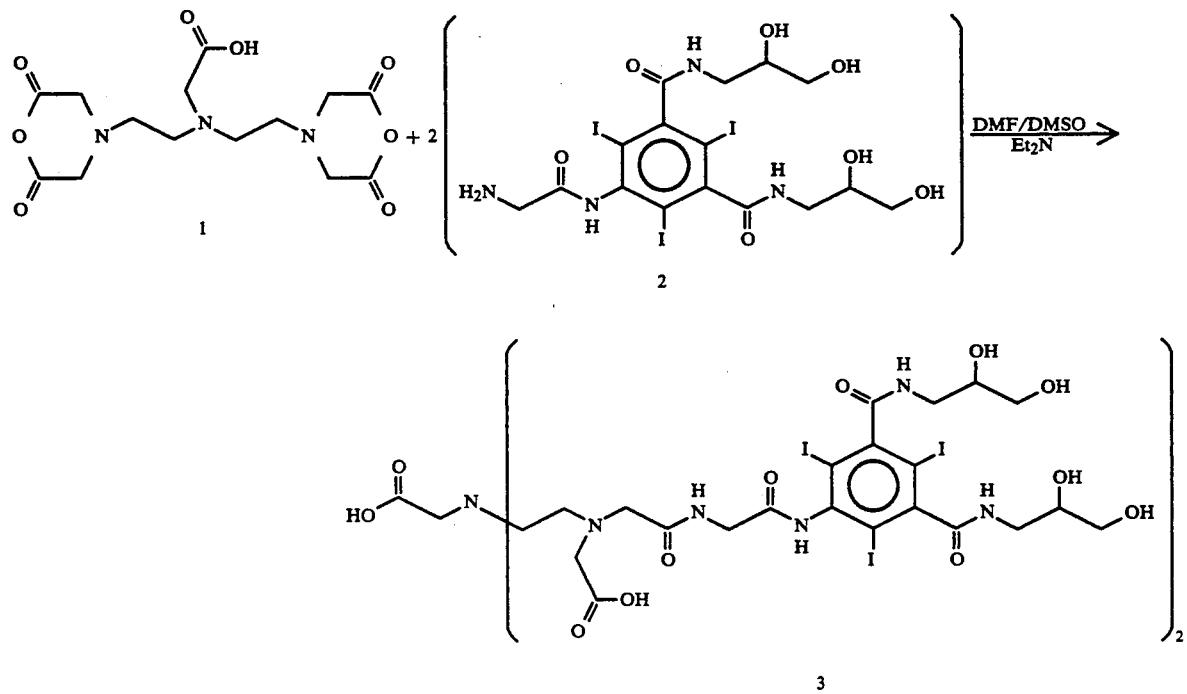

2.35 grams, g., (6.6 mmol.) of N,N-bis[2-(2,6-dioxomorpholino)ethyl]glycine 1, 10.2 g. (13.4 mmol.) of 5-(2-Aminoacetamido)-N,N'-bis(2,3-dihydroxypropyl)-2,4,6-triiodo-isophthalamide 2, and 4.6 milliliter, ml., (3.34 g., 33.0 mmol.) of triethylamine are mixed in 20 product, N,N''-bis{N-{N-[3,5-di(N-(2,3-dihydroxypropyl)carbamoyl)-2,4,6-triiodophenyl]carbamoylmethyl}carbamoylmethyl}-diethylenetriamine-N,N',N''-triacetic acid 3, (2.6 g.).

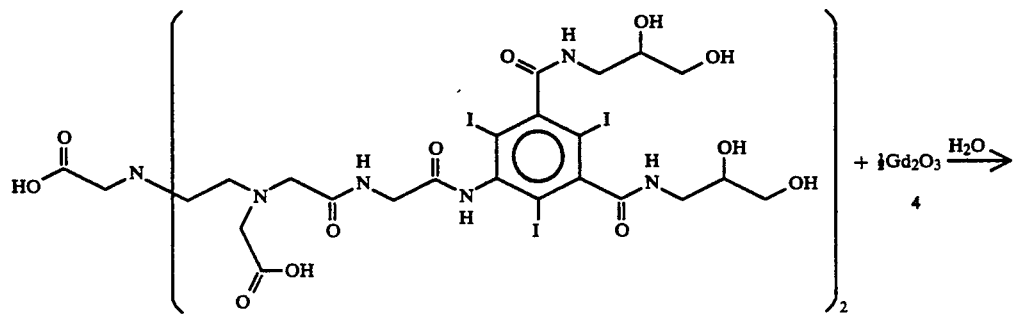

Step 2:

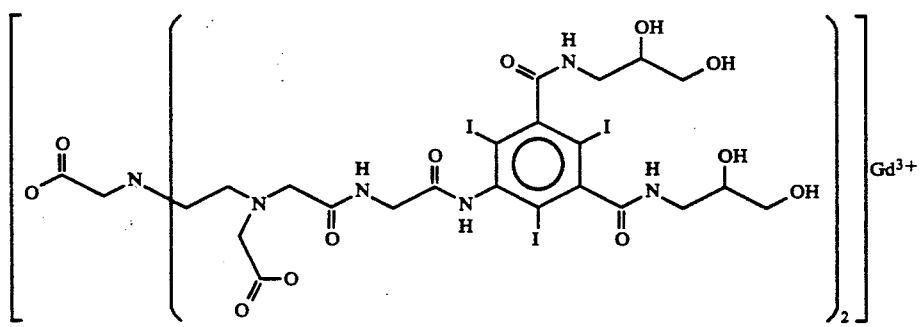

2.0 g. (1.1 mmol.) of 3 and 0.20 g. (0.55 mmol.) of $Gd_2O_3$ 4 and mix in 10 ml. of water and heat at 80° C. for 16 hours. The resulting solution is taken to dryness and purified using preparative high pressure liquid chromatography ($C_{18}$: stationary phase, water: mobile phase) to give a product, [N,N''-bis{N-{N-[3,5-di(N-(2,3-dihydroxypropyl)carbamoyl)-2,4,6-triiodophenyl]-carbamoylmethyl}carbamoylmethyl}-diethylenetriamine-N,N',N''-triaceto]-gadolinium (III) 5.

EXAMPLE 2

Preparation of the Hybrid Compound [N-{N-{-N-[3,5-di(N-(2,3-dihydroxypropyl)carbamoyl)-2,4,6-triiodophenyl]carbamoylmethyl}carbamoylmethyl}-diethylenetriamine-N,N',N''-tetraaceto]-gadolinium (III) (8)

$N^3$-(2,6-dioxomorpholinoethyl) -$N^6$-(ethoxycarbonylmethyl)-3,6-diazaoctan-dioic acid 6, can be prepared according to the procedure described in Journal of Pharmaceutical Science 1979, 68 (2), 194–196 and EP-0 413 405 A2.

2.00 g. (5.3 mmol,) of 6, 4.05 g. (5.3 mmol,) of 2 and 3.7 ml. (2.69 g., 26.6 mmol.) of triethylamine are mixed in 20 ml. of N,N-dimethylformamide and 20 ml, of dimethyl sulfoxide at 0° C. The reaction mixture is then heated at 80° C. for two days to form an adduct, Following that, the adduct is acidified to pH 3.5 and evaporated to a viscous residue. Purification of crude material using preparative high pressure liquid chromatography ( $C_{18}$: stationary phase, water: mobile phase) gives a product, N-{N-{N-[3,5-di(N-(2,3-dihydroxypropyl)carbamoyl)-2,4,6-triiodophenyl]carbamoylmethyl}carbamoylmethyl}-diethylenetriamine-N,N',N'',N'''-tetraacetic acid 7.

Step 1:

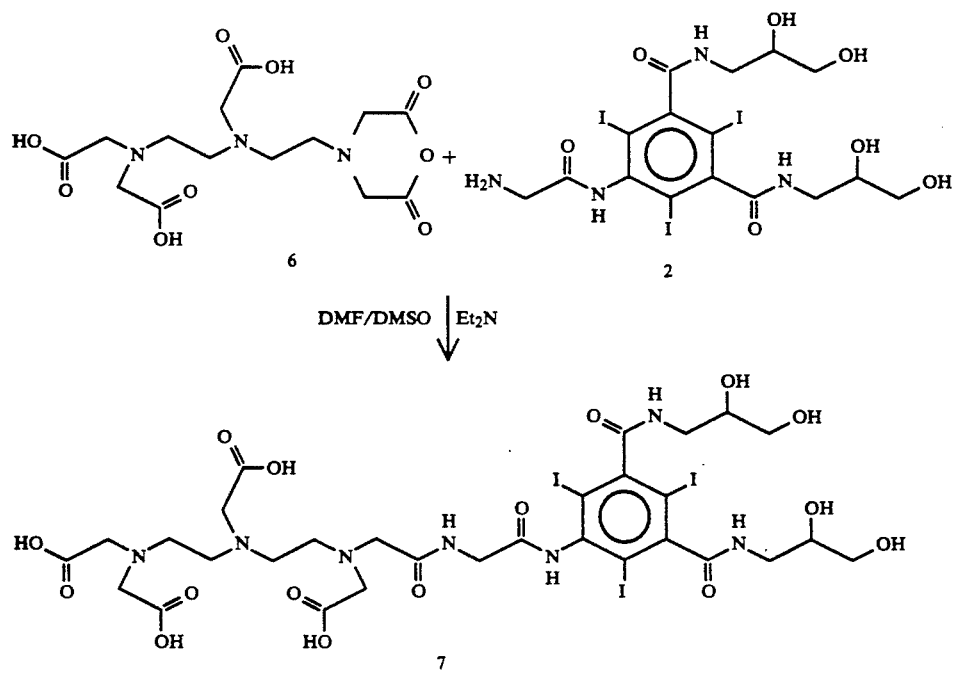

Step 2:

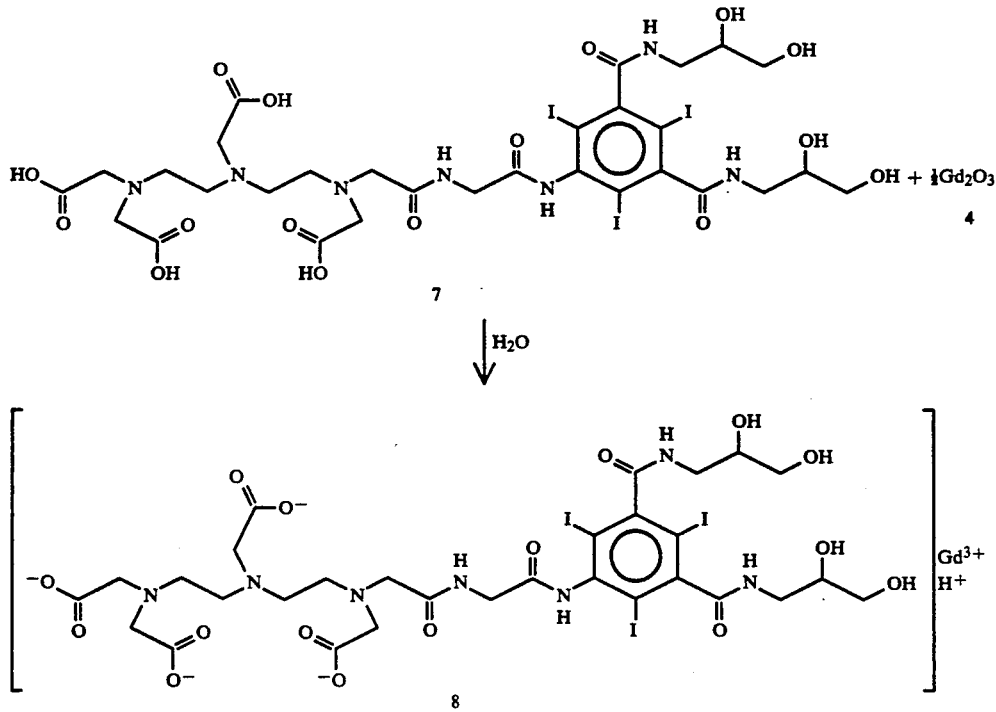

1.5 g. (1.3 mmol.) of 7 and 0.24 g. (0.66 mmol.) of $Gd_2O_3$ 4 are mixed in 10 ml. of water and heated at 80° C. for 16 hours. The resulting solution is taken to dryness and purified using preparative high pressure liquid chromatography ($C_{18}$: stationary phase, water: mobile phase to give a colorless product, [N-{N-{N-[3,5-di{N-(2,3-dihydroxypropyl)carbamoyl)-2,4,6-triiodophenyl]-carbamoylmethyl}carbamoylmethyl}-diethylenetriamine-N,N',N'',N'''-tetraaceto]-gadolinium (III) 8.

The invention is also directed to compositions containing hybrid compounds or methods for utilizing such compounds in x-ray or magnetic resonance imaging (MRI) for diagnostic visualization.

The compounds of the present invention avoid the known osmotic side effects caused by contrast agents having a high osmolality since less may be used for equal or superior image enhancement. Hyperosmolality is known to those skilled in the art to cause vascular pain during the inject ion of many contrast agents. Furthermore, high osmolality has been shown to be an important factor in perturbation of normal heart functions at the time of cardioangiography in warm-blooded animals. However, the main advantage of the hybrid agents of the present invention is low osmolality with concomitant low toxicity. This is achieved by attaching mono- or poly- hydroxyl groups to the agents to increase hydrophilicity thus making the hybrid agents highly soluble compounds while still having three or more iodine atoms and one or more heavy metal ions per molecule as described above. At concentrations of equivalent radio-density, the osmotic effects of the hybrid agent would be less because the number of hybrid molecules would be reduced. The hybrid agents of the present invention thereby provide this advantage while maintaining acceptable solubility characteristics due to the high hydrophilicity of the amine-alcohol side chains.

In further accordance with the present invention, compositions may be prepared containing one or more of the compounds and/or isomers of the aforementioned compounds of the present invention as an imaging agent together with a pharmaceutically acceptable vehicle.

Pharmaceutically acceptable vehicles include those that are suitable for injection such as aqueous buffer solutions; e.g., tris(hydroxymethyl)aminomethane (and its salts), phosphate, citrate, bicarbonate, etc., sterile water for injection, physiological saline, and balanced ionic solutions containing chloride and/or bicarbonate salts of normal blood plasma cations such as calcium, Ca, sodium, Na, potassium, K and magnesium, Mg. Other buffer solutions are described in Remington's Practice of Pharmacy, Eleventh Edition, for example on page 170. The compositions may contain a chelating compound, e.g., a small amount, of ethylenediamine tetraacetic acid, the calcium disodium salt, or other pharmaceutically acceptable salt of a chelating agent.

The concentration of the imaging agents of the present invention in the pharmaceutically acceptable vehicle, for example an aqueous medium, varies with the particular field of use. A sufficient amount is that which provides satisfactory diagnostic visualization. For example, when using aqueous solutions for angiography, the concentration of iodine is generally 140–440 mg/ml and the dose is 25–300 ml.

Parenteral compositions may be injected directly or mixed with a large volume parenteral composition for systemic administration.

Formulations for enteral administration may vary widely, as is well-known in the art. Such enteral compositions may optionally include buffers, surfactants, thixotropic agents, and the like. Compositions for oral administration may also contain flavoring agents and other ingredients for enhancing their organoleptic qualities.

The diagnostic compositions are administered to warm-blooded animals in doses effective to achieve the desired enhancement of the magnetic resonance image or x-ray image. Such doses may vary widely, depending upon the particular compound employed, the organs or tissues which are the subject of the imaging procedure, the MRI or x-ray equipment being used, etc. In general, parenteral dosages will range from about 0.001 to about 1.0 mMol of compound per kg of patient body weight. Preferred parenteral dosages range from about 0.05 to about 0.5 mMol of compound per kg of patient body weight. Enteral dosages generally range from about 0.5 to about 100 mMol, preferably from about 1.0 to about 10 mMol of compound per kg of patient body weight.

The novel contrasting agents of this invention possess a unique combination of desirable features. The compounds exhibit a high solubility in physiological fluids. This high solubility allows the preparation of concentrated solutions, thus minimizing the amount of fluid required to be administered. The hybrid characteristics of the present compounds also reduce the osmolarity of the diagnostic compositions, thus preventing undesired edema and other side effects and improves stability for enhanced safety.

The diagnostic compositions of this invention are used in the conventional manner. The compositions may be administered in a sufficient amount to provide adequate visualization to a warm-blooded animal either systemically or locally to the organ or tissue to be imaged, and the animal then scanned with a suitable MRI machine. The compound(s) of the present invention are administered to the warm-blooded animal so that the compound remains in the living animal body for about 2 to 3 hours, although shorter and longer residence periods are normally acceptable.

Accordingly, having described the invention, we claim:

1. A compound of the formula:

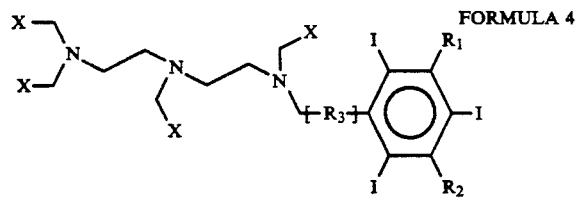

FORMULA 4 wherein
$R_1$ is selected from the group consisting of CONHCH(CH$_2$OH) (CHOHCH$_2$OH), CON(R$_4$)CH$_2$CHOHCH$_2$OH, CON(R$_4$)CH(CH$_2$OH)$_2$, CON(R$_4$)CH$_2$(CH$_2$OH), CON(R$_4$)CH$_3$, CONH$_2$, N(R$_4$)COCH$_2$OH, N(R$_4$)COCH$_3$, CO$_2$R$_5$ and suitable linkers for attaching a biomolecule such as N(R$_4$)COCH$_2$— or N(R$_4$)CS—; $R_2$ is selected from the group consisting of $R_1$,

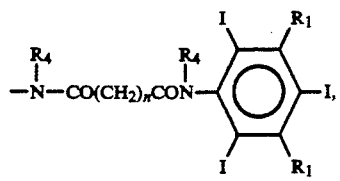

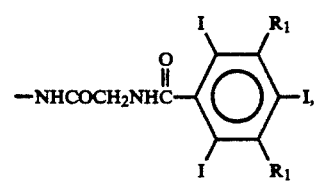

and

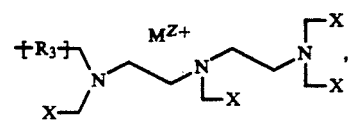

$R_3$ is a linker selected from the group consisting of —N(R$_4$)CO(CH$_2$)$_m$NHCO, —N(R$_4$)CO, CONHCH$_2$(CH$_2$)$_m$NHCO, N(R$_4$)COCH$_2$— and N(R$_4$)CS—;

$R_4$ is selected from the group consisting of hydrogen, C$_{1-10}$ alkyl, C$_{1-10}$ mono- or poly- hydroxyalkyl and C$_{1-10}$ mono- or poly- alkoxyalkyl;

$R_5$ is selected from the group consisting of cations such as sodium, potassium, meglumine and quaternary ammonium compounds;

X is a ligand chelating site selected from the group consisting of —CO$_2$—, CH$_2$S—, —PO$_3$—, —CONHCH$_2$CHOHCH$_2$OH, —CONHOH, —CONHCH$_2$CO$_2$—, phenolate and Y;

Y is selected from the group consisting of

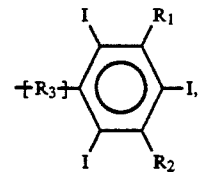

COQ and CONHQ;

Q is selected from the group consisting of biomolecules and polyhydroxyl compounds;

$M^{z+}$ is a heavy metal ion selected from the group consisting of Bi, Gd, Ba, Gd, Mn, Cu, Cr, Fe, Co, Er, Ni, Eu, Dy, Sc, Ti, V, Mo, Tc, Ru, Ce, Pt, Nd, Pm, Sm, Tb, Ho, Tm, and Yb having a valence z of 2+, 3+ or 4+;

n is a whole number less than eleven; and m is an integer less than eleven.

2. A compound of the formula:

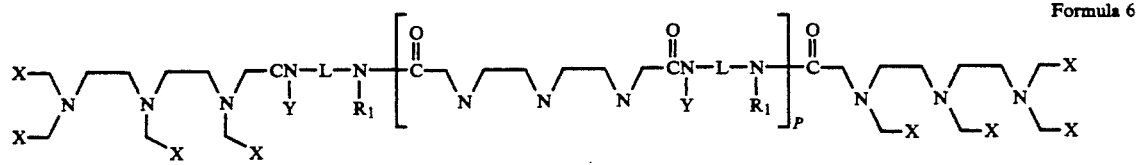

Formula 6 wherein

Y is selected from the group consisting of

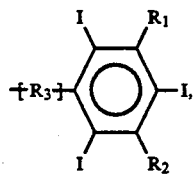

COQ and CONHQ, wherein at least one Y is

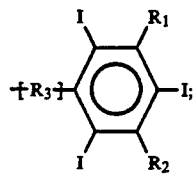

$R_1$ is selected from the group consisting of CONHCH($CH_2OH$)(CHOHCH$_2$OH), CON($R_4$)CH$_2$CHOHCH$_2$OH, CON($R_4$)CH(CH$_2$OH)$_2$, CON($R_4$)CH$_2$(CH$_2$OH), CON($R_4$)CH$_3$, CONH$_2$, N($R_4$)COCH$_2$OH, N($R_4$)COCH$_3$, CO$_2$R$_5$ and suitable linker for attaching a biomolecule such as N($R_4$)COCH$_2$— or N($R_4$)CS—; $R_2$ is selected from the group consisting of $R_1$,

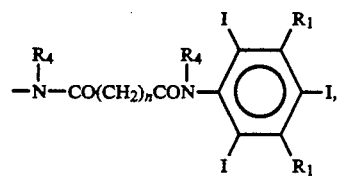

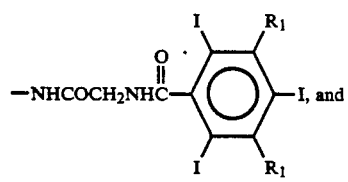

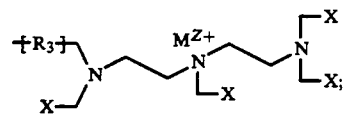

$R_3$ is a linker selected from the group consisting of —N($R_4$)CO(CH$_2$)$_m$NHCO, —N($R_4$)CO, CONHCH$_2$(CH$_2$)$_m$NHCO, N($R_4$)COCH$_2$— and N($R_4$)CS—;

$R_4$ is selected from the group consisting of hydrogen, $C_{1-10}$ alkyl, $C_{1-10}$ mono- or poly- hydroxyalkyl and $C_{1-10}$ mono- or poly- alkoxyalkyl;

$R_5$ is selected from the group consisting of cations such as sodium, potassium, meglumine and quaternary ammonium compounds;

X is a ligand chelating site selected from the group consisting of —CO$_2$—, CH$_2$S—, —PO$_3$—, —CONHCH$_2$CHOHCH$_2$OH, —CONHOH, —CONHCH$_2$CO$_2$—, phenolate and Y;

Q is selected from the group consisting of biomolecules and polyhydroxyl compounds;

$M^{z+}$ is a heavy metal ion selected from the group consisting of Bi, Gd, Ba, Gd, Mn, Cu, Cr, Fe, Co, Er, Ni, Eu, Dy, Sc, Ti, V, Mo, Tc, Ru, Ce, Pt, Nd, Pm, Sm, Tb, Ho, Tm and Yb having a valence z of 2+, 3+ or 4+;

n is a whole number less than eleven; and m is an integer less than eleven;

L is a linker selected from the group consisting of —(CH$_2$CH$_2$O)$_n$CH$_2$CH$_2$—, —CH$_2$—(CHOH)$_n$—CH$_2$—, and —(CH$_2$)$_n$—; and p is an integer less than 500.

3. A diagnostic composition suitable for administration to a warm-blooded animal, which comprises an effective amount of the agent having the following formula

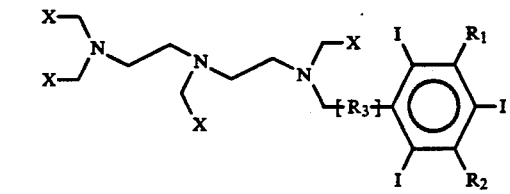

where $R_1$ is selected from the group consisting of CONHCH(CH$_2$OH)(CHOHCH$_2$OH), CON($R_4$)CH$_2$CHOHCH$_2$OH, CON($R_4$)CH(CH$_2$OH)$_2$, CON($R_4$)CH$_2$(CH$_2$OH), CON($R_4$)CH$_3$, CONH$_2$, N($R_4$)COCH$_2$OH, N($R_4$)COCH$_3$, CO$_2$R$_5$ and suitable linkers for attaching a biomolecule such as N($R_4$)COCH$_2$— or N($R_4$)CS—; $R_2$ is selected from the group consisting of $R_1$,

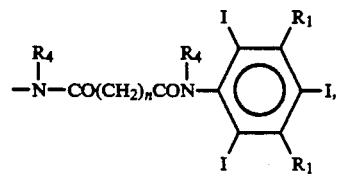

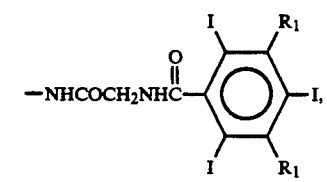

and

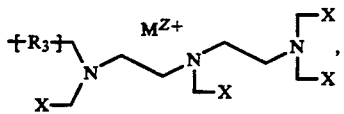

$R_3$ is a linker selected from the group consisting of —N($R_4$)CO(CH$_2$)$_m$NHCO, —N($R_4$)CO, CONHCH$_2$(CH$_2$)$_m$NHCO, N($R_4$)COCH$_2$— and N($R_4$)CS—;

$R_4$ is selected from the group consisting of hydrogen, $C_{1-10}$ alkyl, $C_{1-10}$ mono- or poly- hydroxyalkyl and $C_{1-10}$ mono- or poly- alkoxyalkyl;

$R_5$ is selected from the group consisting of cations such as sodium, potassium, meglumine and quaternary ammonium compounds;

X is a ligand chelating site selected from the group consisting of —CO$_2$—, CH$_2$S—, —PO$_3$—, —CONHCH$_2$CHOHCH$_2$OH, —CONHOH, —CONHCH$_2$CO$_2$—, phenolate and Y;

Y is selected from the group consisting of

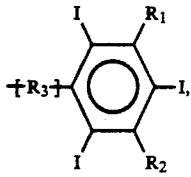

COQ and CONHQ;

Q is selected from the group consisting of biomolecules and polyhydroxyl compounds;

$M^{z+}$ is a heavy metal ion selected from the group consisting of Bi, Gd, Ba, Gd, Mn, Cu, Cr, Fe, Co, Er, Ni, Eu, Dy, Sc, Ti, V, Mo, Tc, Ru, Ce, Pt, Nd, Pm, Sm, Tb, Ho, Tm and Yb having a valence z of 2+, 3+ or 4+;

n is a whole number less than eleven; m is an integer less than eleven; and a pharmaceutically acceptable carrier.

4. A diagnostic composition suitable for administration to a warm-blooded animal, which comprises an effective amount of the agent having the following formula

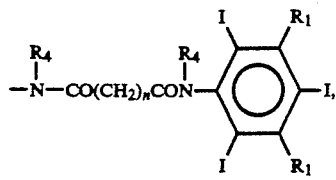

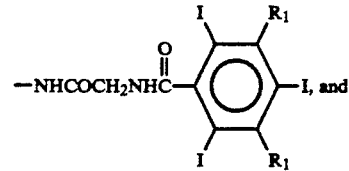

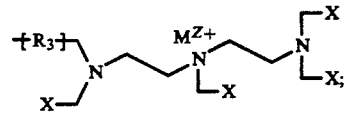

$R_3$ is a linker selected from the group consisting of $-N(R_4)CO(CH_2)_mNHCO$, $-N(R_4)CO$, $CONHCH_2(CH_2)_mNHCO$, $N(R_4)COCH_2-$ and

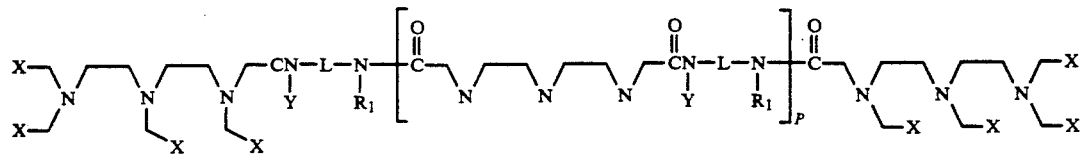

where
Y is selected from the group consisting of

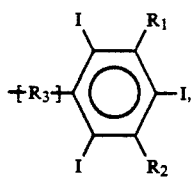

COQ and CONHQ, wherein at least one Y is

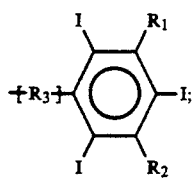

$R_1$ is selected from the group consisting of $CON(R_4)CH_2CHOHCH_2OH$, $CON(R_4)CH_2(CH_2OH)_2$, $CON(R_4)CH_2(CH_2OH)$, $CON(R_4)CH_3$, $CONH_2$, $N(R_4)COCH_2OH$, $N(R_4)COCH_3$, $CO_2R_5$ and suitable linkers for attaching a biomolecule such as $N(R_4)COCH_2-$ or $N(R_4)CS-$; $R_2$ is selected from the group consisting of $R_1$, $N(R_4)CS-$;

$R_4$ is selected from the group consisting of hydrogen, $C_{1-10}$ alkyl, $C_{1-10}$ mono- or poly-- hydroxyalkyl and $C_{1-10}$ mono- or poly- alkoxyalkyl;

$R_5$ is selected from the group consisting of cations such as sodium, potassium, meglumine and quaternary ammonium compounds;

X is a ligand chelating site selected from the group consisting of $-CO_2^-$, $CH_2S^-$, $-PO_3^-$, $-CONHCH_2CHOHCH_2OH$, $-CONHOH$, $-CONHCH_2CO_2^-$, phenolate and Y;

Q is selected from the group consisting of biomolecules and polyhydroxyl compounds;

$M^{z+}$ is a heavy metal ion selected from the group consisting of Bi, Gd, Ba, Gd, Mn, Cu, Cr, Fe, Co, Er, Ni, Eu, Dy, Sc, Ti, V, Mo, Tc, Ru, Ce, Pt, Nd, Pm, Sm, Tb, Ho, Tm and Yb having a valence z of 2+, 3+ or 4+;

L is a linker selected from the group consisting of $-(CH_2CH_2O)_nCH_2CH_2-$, $-CH_2-(CHOH)_n-CH_2-$, and $-(CH_2)_n-$;

n is a whole number less than eleven; m is an integer less than eleven; p is an integer of 500 or less; and a pharmaceutically acceptable carrier.

5. A method of performing an x-ray image enhancing diagnostic procedure which comprises administering to a warm-blooded animal a x-ray-effective amount of an agent of the formula

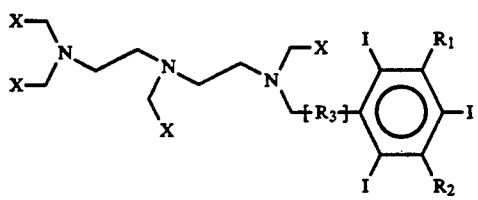

wherein
$R_1$ is selected from the group consisting of
CONHCH($CH_2OH$)(CHOHCH$_2$OH),
CON($R_4$)CH$_2$CHOHCH$_2$OH, CON($R_4$)CH(CH$_2$OH)$_2$, CON($R_4$)CH$_2$(CH$_2$OH), CON($R_4$)CH$_3$, CONH$_2$, N($R_4$)COCH$_2$OH, N($R_4$)COCH$_3$, $CO_2^-R_5$ and suitable linkers for attaching a biomolecule such as N($R_4$)COCH$_2$— or N($R_4$) CS—;
$R_2$ is selected from the group consisting of $R_1$,

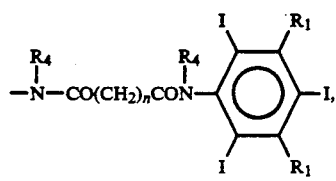

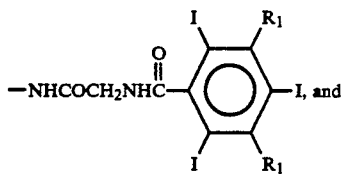

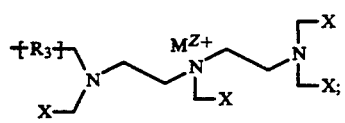

$R_3$ is a linker selected from the group consisting of
—N($R_4$)CO(CH$_2$)$_m$NHCO, —N($R_4$)CO, CONHCH$_2$(CH$_2$)$_m$NHCO, N($R_4$)COCH$_2$— and N($R_4$)CS—;
$R_4$ is selected from the group consisting of hydrogen, $C_{1-10}$ alkyl, $C_{1-10}$ mono- or poly-hydroxyalkyl and $C_{1-10}$ mono- or poly- alkoxyalkyl;
$R_5$ is selected from the group consisting of cations such as sodium, potassium, meglumine and quaternary ammonium compounds;
X is a ligand chelating site selected from the group consisting of —CO$_2^-$, CH$_2$S$^-$, —PO$_3^-$, —CONHCH$_2$CHOHCH$_2$OH, —CONHOH, —CONHCH$_2$CO$_2^-$, phenolate and Y;
Y is selected from the group consisting of COQ and CONHQ;
Q is selected from the group consisting of biomolecules and polyhydroxyl compounds;
$M^{z+}$ is a heavy metal ion selected from the group consisting of Bi, Gd, Ba, Gd, Mn, Cu, Cr, Fe, Co, Er, Ni, Eu, Dy, Sc, Ti, V, Mo, Tc, Ru, Ce, Pr, Nd, Pm, Sm, Tb, Ho, Tm and Yb having a valence z of 2+, 3+ or 4+;
n is a whole number less than eleven; m is an integer less than eleven; and a pharmaceutically acceptable carrier; and then exposing the animal to a x-ray procedure, thereby imaging at least a portion of said warm-blooded animal.

6. A method of performing an x-ray image enhancing diagnostic procedure which comprises administering to a warm-blooded animal a x-ray-effective amount of an agent of the formula

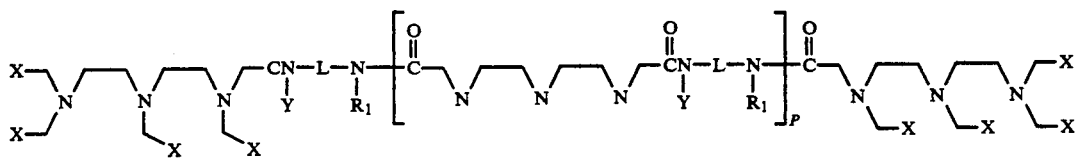

wherein
Y is selected from the group consisting of

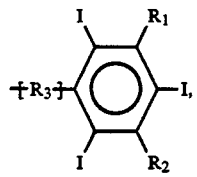

COQ and CONHQ, wherein at least one Y is

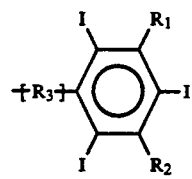

$R_1$ is selected from the group consisting of
CONHCH(CH$_2$OH)(CHOHCH$_2$OH),
CON($R_4$)CH$_2$CHOHCH$_2$OH, CON($R_4$)CH(CH$_2$OH)$_2$, CON($R_4$)CH$_2$(CH$_2$OH ), CON($R_4$)CH$_3$, CONH$_2$, N($R_4$)COCH$_2$OH, N($R_4$)COCH$_3$, $CO_2^-R_5$ and suitable linkers for attaching a biomolecule such as N($R_4$)COCH$_2$— or N($R_4$)CS—;
$R_2$ is selected from the group consisting of $R_1$;

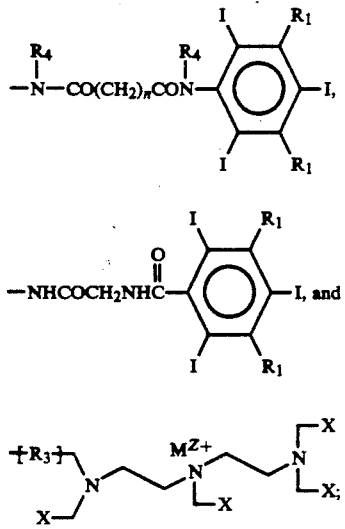

$R_3$ is a linker selected from the group consisting of —N($R_4$)CO(CH$_2$)$_m$NHCO, —N($R_4$)CO-CONHCH$_2$(CH$_2$)$_m$NHCO, N($R_4$)COCH$_2$— and N($R_4$)CS—;

$R_4$ is selected from the group consisting of hydrogen, $C_{1-10}$ alkyl, $C_{1-10}$ mono- or poly- hydroxyalkyl and $C_{1-10}$ mono- or poly- alkoxyalkyl;

$R_5$ is selected from the group consisting of cations such as sodium, potassium, meglumine and quaternary ammonium compounds;

X is a ligand chelating site selected from the group consisting of —CO$_2^-$, CH$_2$S$^-$, —PO$_3^-$, —CONHCH$_2$CHOHCH$_2$OH, —CONHOH, —CONHCH$_2$CO$_2^-$, phenolate and Y;

Q is selected from the group consisting of biomolecules and polyhydroxyl compounds;

$M^{z+}$ is a heavy metal ion selected from the group consisting of Bi, Gd, Ba, Gd, Mn, Cu, Cr, Fe, Co, Er, Ni, Eu, Dy, Sc, Ti, V, Mo, Tc, Ru, Ce, Pt, Nd, Pm, Sm, Tb, Ho, Tm and Yb having a valence z of 2+, 3+ or 4+;

L is a linker selected from the group consisting of —(CH$_2$CH$_2$O)$_n$CH$_2$CH$_2$—, —CH$_2$—(CHOH)$_n$—CH$_2$—, and —(CH$_2$)$_n$—;

n is a whole number less than eleven; m is an integer less than eleven; p is an integer of 500 or less; and a pharmaceutically acceptable carrier; and then exposing the animal to a x-ray procedure, thereby imaging at least a portion of said warm-blooded animal.

* * * * *